(12) United States Patent
Sieh et al.

(10) Patent No.: US 12,279,786 B2
(45) Date of Patent: Apr. 22, 2025

(54) RETRACTABLE SHAVER BUR

(71) Applicant: Conmed Corporation, Utica, NY (US)

(72) Inventors: John K. Sieh, Safety Harbor, FL (US);
Ronald D. Woodring, Dunedin, FL (US); Steven T. Helak, Tampa, FL (US); John F. Collins, Tampa, FL (US)

(73) Assignee: Conmed Corporation, Utica, NY (US)

( * ) Notice: Subject to any disclaimer, the term of this patent is extended or adjusted under 35 U.S.C. 154(b) by 856 days.

(21) Appl. No.: 17/413,320

(22) PCT Filed: Dec. 9, 2019

(86) PCT No.: PCT/US2019/065143
§ 371 (c)(1),
(2) Date: Jun. 11, 2021

(87) PCT Pub. No.: WO2020/123335
PCT Pub. Date: Jun. 18, 2020

(65) Prior Publication Data
US 2022/0039819 A1 Feb. 10, 2022

Related U.S. Application Data

(60) Provisional application No. 62/779,031, filed on Dec. 13, 2018.

(51) Int. Cl.
*A61B 17/16* (2006.01)
*A61B 17/32* (2006.01)
*A61B 17/00* (2006.01)

(52) U.S. Cl.
CPC .... *A61B 17/32002* (2013.01); *A61B 17/1604* (2013.01); *A61B 2017/00876* (2013.01); *A61B 2017/320028* (2013.01)

(58) Field of Classification Search
CPC ........ A61B 17/320016; A61B 17/1604; A61B 17/1633
See application file for complete search history.

(56) References Cited

U.S. PATENT DOCUMENTS 2,525,669 A * 10/1950 Hainault ............ A61B 17/1695
408/140
3,216,288 A * 11/1965 Gardner ................. B23D 77/12
30/162

(Continued)

FOREIGN PATENT DOCUMENTS

| CN | 106999202 A | 8/2017 |
| WO | 2012/112649 | 8/2012 |

OTHER PUBLICATIONS

Chinese Office Action, Application No. 201980082945.3, dated Aug. 29, 2023, pp. 1-9.

(Continued)

*Primary Examiner* — Nicholas W Woodall
(74) *Attorney, Agent, or Firm* — Bond, Schoeneck & King, PLLC; Frederick J. M. Price (57) ABSTRACT

A shaver bur for resecting bone inside the joint in arthroscopic procedures. The shaver bur includes an inner assembly having an inner hub with an inner tube extending distally therefrom. The inner tube terminates in a distal bur tip. The shaver bur also includes an outer assembly having an outer hub with an outer tube extending distally therefrom. The inner tube is moveable within the outer tube between a retracted position and an extended position. The shaver bur additionally includes a deployment mechanism connected to the outer hub. The deployment mechanism is movable in a first direction and a second direction. Moving the deployment mechanism in the first direction moves the inner tube to the extended position and moving the deployment mecha- (Continued)

nism in the second direction moves the inner tube to the retracted position.

6 Claims, 7 Drawing Sheets

(56) References Cited

U.S. PATENT DOCUMENTS

| | | | | |
|---|---|---|---|---|
| 3,682,177 | A | * | 8/1972 | Ames ................. A61B 17/1695 408/202 |
| 4,733,662 | A | * | 3/1988 | DeSatnick ..... A61B 17/320016 30/162 |
| 5,527,331 | A | * | 6/1996 | Kresch ............... A61B 18/1485 606/45 |
| 5,667,509 | A | * | 9/1997 | Westin ............... A61B 17/1633 606/80 |
| 5,817,111 | A | | 10/1998 | Riza |
| 8,088,135 | B2 | | 1/2012 | Heisler |
| 8,784,421 | B2 | | 7/2014 | Carrison et al. |
| 9,717,507 | B2 | | 8/2017 | Patel et al. |
| 10,433,856 | B2 | | 10/2019 | Prescott |
| 10,441,295 | B2 | | 10/2019 | Brockman et al. |
| 2001/0016744 | A1 | * | 8/2001 | Kupferschmid ... A61B 17/1695 606/80 |
| 2006/0259055 | A1 | | 11/2006 | Thorne et al. |
| 2008/0021487 | A1 | | 1/2008 | Heisler |
| 2010/0198242 | A1 | * | 8/2010 | Heisler ............ A61B 17/32002 606/170 |
| 2013/0072935 | A1 | | 3/2013 | Matsuda et al. |

OTHER PUBLICATIONS

AU Examination Report, Application No. 2022256156, dated Sep. 22, 2023, pp. 1-3.
International Search Report Form PCT/ISA/220, International Application No. PCT/US2019/065143, pp. 1-16, Dated Mar. 9, 2020.
KR Office Action, Application No. 10-2021-7019002, dated Jun. 20, 2023, pp. 1-6.

* cited by examiner

RETRACTABLE SHAVER BUR

CROSS-REFERENCES TO RELATED APPLICATIONS

This application is a national stage application under 35 U.S.C. 371 based on international patent application PCT/US19/65143 filed on Dec. 9, 2019, which claims priority to U.S. Provisional Patent Application Ser. No. 62/779,031 filed on Dec. 13, 2018, the entireties of which are incorporated herein by reference.

BACKGROUND OF THE INVENTION

1. Field of the Invention

The present invention relates to a surgical cutting device and, more particularly, to a shaver bur having a retractable bur tip.

2. Description of Related Art

Shaver burs are surgical cutting instruments having a sharp flute intended to "shave" or resect bone inside the joint during arthroscopic procedures. Surgical shaver burs are comprised of an inner and an outer assembly. The outer assembly is composed of a hollow steel tube, which is bonded to a molded plastic hub on the proximal end and contains a cut out or open hood on the distal end. The inner assembly is housed within the outer assembly and comprises an inner tube. The inner tube is composed of a hollow steel tube, which is bonded to a molded plastic hub on the proximal end and welded to a shaver bur tip on the distal end.

In use, the bur tip will spin forward, backward, or oscillate while the outer assembly remains stationary. In traditional shaver burs, the bur tip is permanently exposed. As a result, during arthroscopic procedures, the sharp cutting edges of the bur trip occasionally and unintentionally contact articular surfaces within the joint space. This contact can cause damage and injury to the patient at the surgical site.

Therefore, there is a need for a shaver bur with a protectable bur tip to improve operation conditions.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

The present disclosure is directed to a shaver bur for resecting bone inside the joint in arthroscopic procedures. According to an aspect, the shaver bur includes an inner assembly having an inner hub with an inner tube extending distally therefrom. The inner tube terminates in a distal bur tip. The shaver bur also includes an outer assembly having an outer hub with an outer tube extending distally therefrom. The inner tube is moveable within the outer tube between a retracted position and an extended position. The shaver bur additionally includes a deployment mechanism connected to the outer hub. The deployment mechanism is movable in a first direction and a second direction. Moving the deployment mechanism in the first direction moves the inner tube to the extended position and moving the deployment mechanism in the second direction moves the inner tube to the retracted position.

According to another aspect, the shaver bur includes an inner assembly having an inner hub with an inner tube extending distally therefrom. The inner tube terminates in a distal bur tip. The shaver bur also includes an outer assembly having an outer hub with an outer tube extending distally therefrom. The inner tube is moveable within the outer tube between a retracted position and an extended position. The shaver bur additionally includes a magnet retainer connected between the inner hub and the outer hub. The shaver bur has a deployment mechanism connected to the outer hub. The deployment mechanism is movable in a first direction and a second direction. Moving the deployment mechanism in the first direction moves the inner tube to the extended position and moving the deployment mechanism in the second direction moves the inner tube to the retracted position. In addition, moving the deployment mechanism in the second direction moves the deployment mechanism against the magnet retainer.

According to yet another aspect, the present invention is a method for resecting bone. The method includes the steps of: (i) providing a shaver bur including an inner assembly having an inner hub with an inner tube extending distally therefrom, the inner tube terminating in a distal bur tip, an outer assembly having an outer hub with an outer tube extending distally therefrom, wherein the inner tube is within the outer tube, and a deployment mechanism connected to the outer hub; (ii) moving the deployment mechanism in a first direction, causing the distal bur tip to extend from the outer tube; (iii) resecting bone with the distal bur tip; and (iv) moving the deployment mechanism is a second direction, causing the distal bur tip to be retracted into the outer tube.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Figure 1:
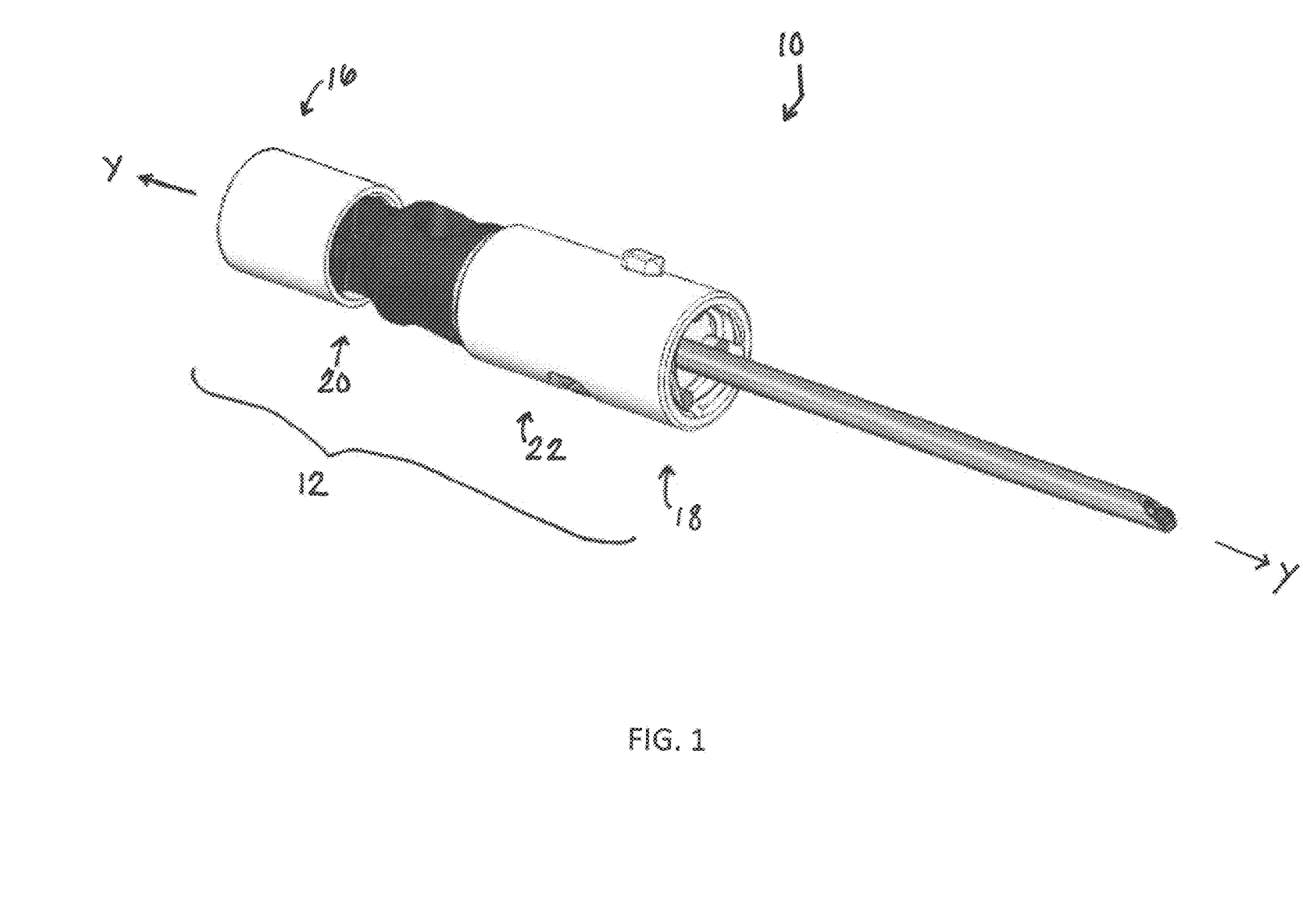
FIG. 1 is a perspective view schematic representation of the shaver bur, according to an embodiment.

Referring now to the drawings, wherein like reference numerals refer to like parts throughout, there is seen in FIG. 1, a perspective view schematic representation of a retractable shaver bur 10, according to an embodiment. The shaver bur 10 includes a proximal outer hub assembly 12 with an outer tube 14 (see, also FIG. 3) extending distally therefrom along a central longitudinal y-y axis. The outer hub assembly 12 extends to and comprises a proximal end 16 and the outer tube 14 extends to and comprises a distal end 18 of the shaver bur 10, as shown in FIG. 1. The shaver bur 10 comprises a proximal inner assembly 20 coupled to a distal outer assembly 22.

Figure 2:
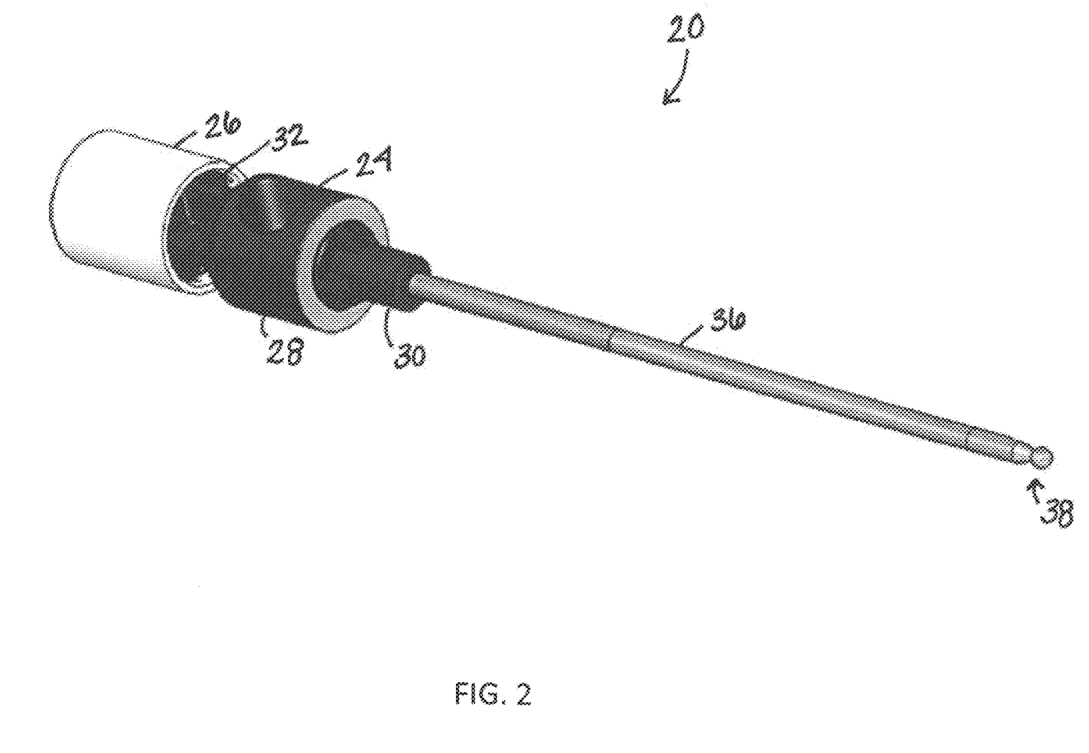
FIG. 2 is a perspective view schematic representation of the inner assembly of the shaver bur, according to an embodiment.

Turning now to FIG. 2, there is shown a perspective view schematic representation of the inner assembly 20 of the shaver bur 10, according to an embodiment. The inner assembly 20 includes an inner hub 24 connected to a proximal end cap 26. In an embodiment, the proximal end cap 26 is removably attached to the inner hub 24. In an alternative embodiment, the proximal end cap 26 is bonded to the inner hub 24. As shown in FIG. 2, the inner hub 24 and the proximal end cap 26 are substantially cylindrical.

Figure 4:
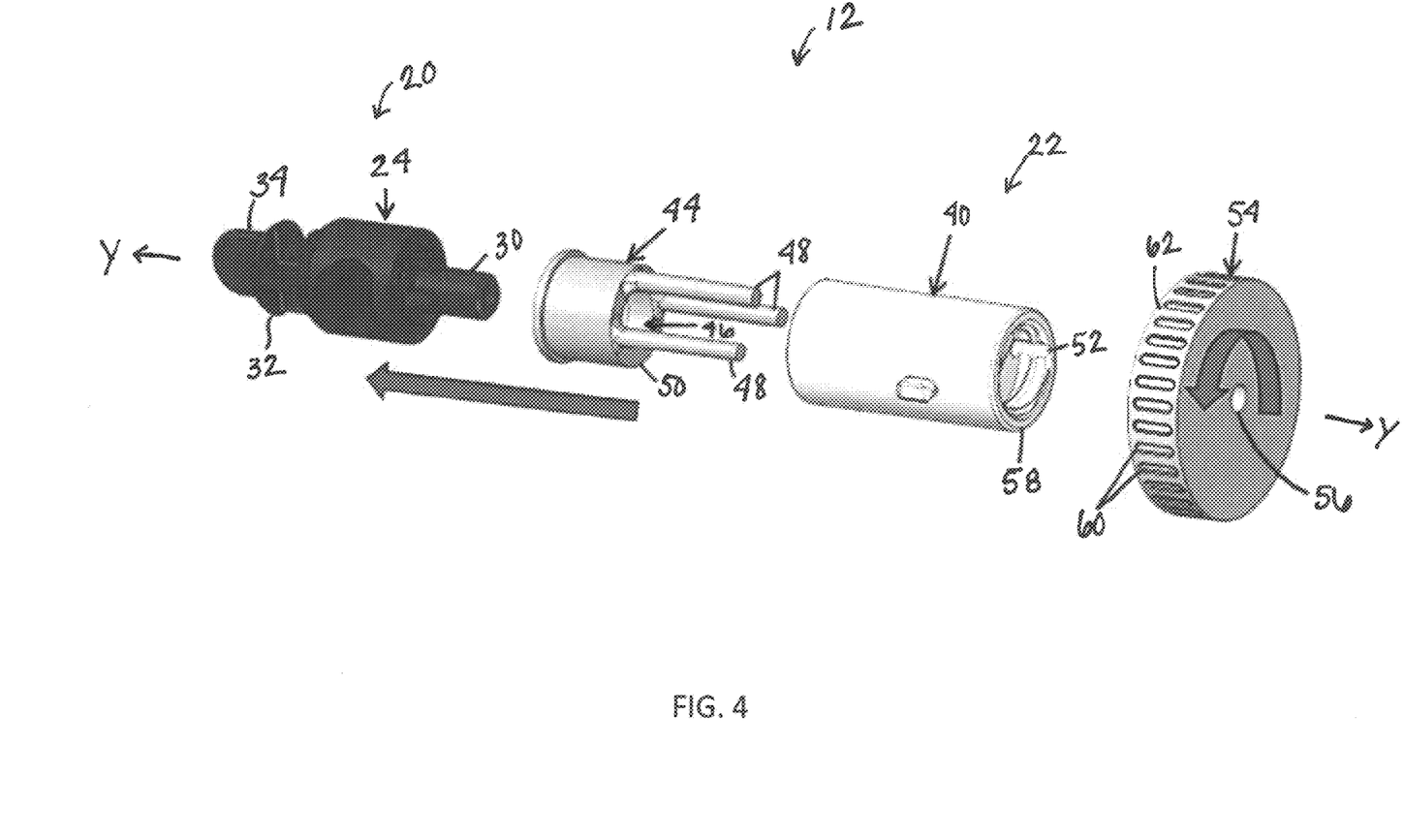
FIG. 4 is an exploded perspective view schematic representation of the outer hub assembly of the shaver bur, according to an embodiment.

Still referring to FIG. 2, the inner hub 24 comprises a cylindrical central body 28 with a central connecting tube 30 extending therefrom in the distal direction. The inner hub 24 also includes a key portion 32 extending from the central body 28 in the proximal direction. The key portion 32 includes one or more features 34 for connecting the inner hub 24 to the proximal end cap 26 (FIG. 4). As shown in FIG. 2, the inner hub 24 is connected to an inner tube 36. The central connecting tube 30 extending distally from the inner hub 24 is cannulated and configured or otherwise adapted to receive the inner tube 36, as shown in FIG. 2. In the depicted embodiment, the inner tube 36 is solid. The inner tube 36 can be composed of steel and/or other similar hard metals. The inner tube 36 extends to and includes a distal bur tip 38. The bur tip 38 is used to shave or resect bone inside a joint during arthroscopic procedures.

Figure 3:
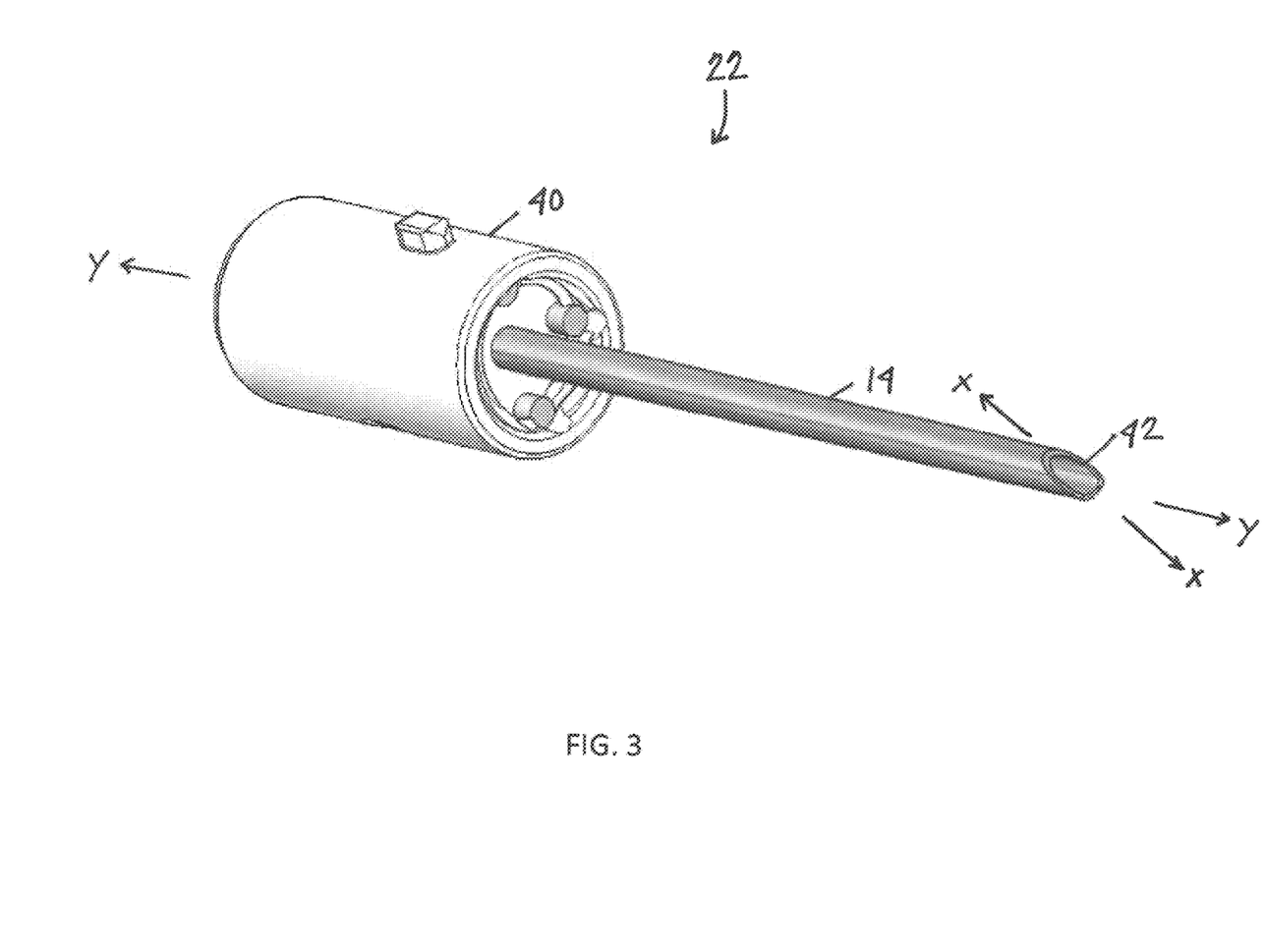
FIG. 3 is a perspective view schematic representation of the outer assembly of the shave bur, according to an embodiment.

Referring now to FIG. 3, there is shown a perspective view schematic representation of the outer assembly 22 of the shaver bur 10, according to an embodiment. The outer assembly 22 includes a cylindrical outer hub 40 connected to the cannulated outer tube 14. As recited above, the cannulated outer tube 14 extends distally from the outer hub 40. In an embodiment, the outer hub 40 is bonded to the cannulated outer tube 14. The cannulated outer tube 14 comprises an open distal end 42. In the depicted embodiment, the open distal end 42 is angled such that a plane x-x extending over the open distal end 42 is at an angle relative to the central longitudinal y-y axis. In the depicted embodiment, the plane a-a is at an angle less than 90 degrees relative to the central longitudinal y-y axis.

Turning now to FIG. 4, there is shown an exploded perspective view schematic representation of the outer hub assembly 12, according to an embodiment. As described above, the outer hub assembly 12 includes the inner hub 24 of the inner assembly 20 and the outer hub 40 of the outer assembly 22. Between the inner hub 24 and the outer hub 40 is a magnet retainer 44. The magnet retainer 44 is cylindrical with a central bore 46 extending therethrough. The magnet retainer 44 additionally comprises one or more stems 48 (e.g., rods) extending distally therefrom. As shown in FIG. 4, the stems 48 extend from a distal end 50 of the magnet retainer 44 toward the outer hub 40. The purpose of the magnetic retainer 44 is to allow for identification of the type of blade or bur used with a handpiece (not shown) connected to the outer hub assembly 12. The magnetic retainer 44 can convey information to the handpiece and connected control system (not shown) so that appropriate signals may be generated by the control system to optimize attachments for certain procedures requiring varying speeds and torques. The signals may also alter the operation of buttons on the handpiece (e.g., toggle, momentary on/off, etc.).

Figure 5:
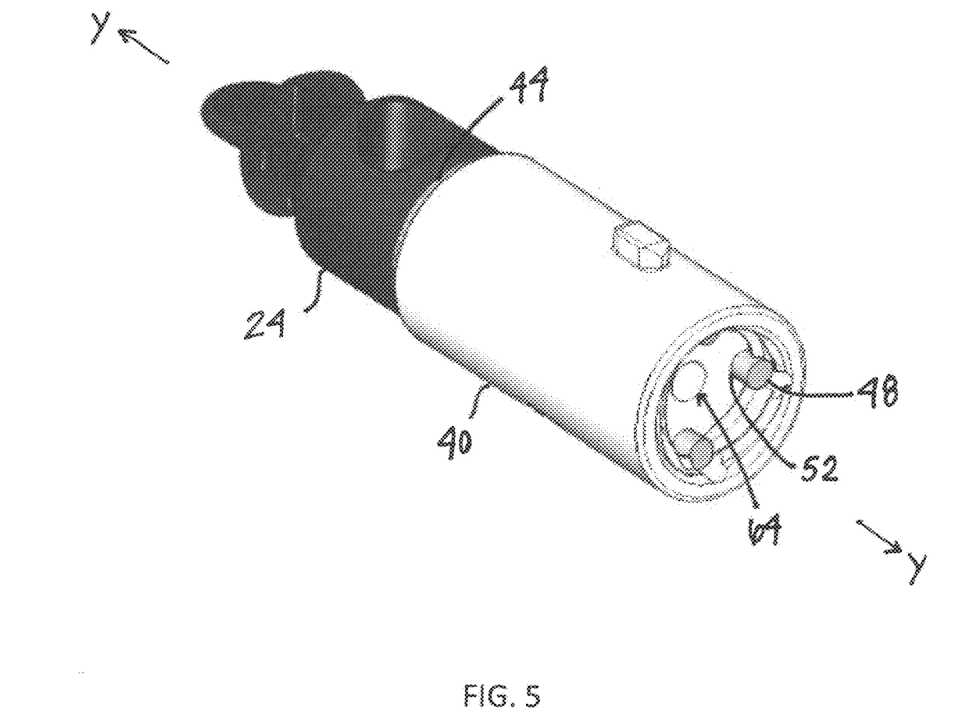
FIG. 5 is a perspective view schematic representation of the inner hub coupled to the outer hub, according to an embodiment.

Referring briefly to FIG. 5, there is shown a perspective view schematic representation of the inner hub 24 coupled to the outer hub 40, according to an embodiment. As shown in FIG. 5, the inner hub 24 is coupled to the outer hub 40 with the magnet retainer 44 therebetween. The outer hub 40 comprises one or more slots 52 extending at least partially therethrough along the central longitudinal y-y axis (FIG. 4). In the depicted embodiment, the slots 52 extend entirely through the outer hub 40. When the outer hub assembly 12 is assembled, the central connecting tube 30 of the inner hub 24 extends through the central bore 46 of the magnet retainer 44 (FIG. 4). The one or more stems 48 of the magnet retainer 44 extend into the one or more slots 52 of the outer hub 40. The outer hub 40 includes a central bore 64 configured or otherwise adapted to receive the inner tube 36.

Turning back to FIG. 4, the outer hub assembly 12 additionally comprises a deployment mechanism 54. In the depicted embodiment, the deployment mechanism 54 is a "twist ring." The twist ring 54 is a rotatable circular piece, such as a disk, cap, or plate. In the depicted embodiment, the twist ring 54 is a rotatable, cylindrical disk with a central bore 56 extending therethrough. The twist ring 54 is attached to a distal end 58 of the outer hub 40 and abuts (or is adjacent to) the one or more stems 48 of the magnet retainer 44. The twist ring 54 functions to extend and retract the distal bur tip 38 (FIG. 1). In the embodiment in FIG. 4, the twist ring 54 comprises a plurality of ridges 60 extending along its outer circumference 62. The ridges 60 allow a user to get a firm grip on the twist ring 54 to rotate it.

Figure 6:
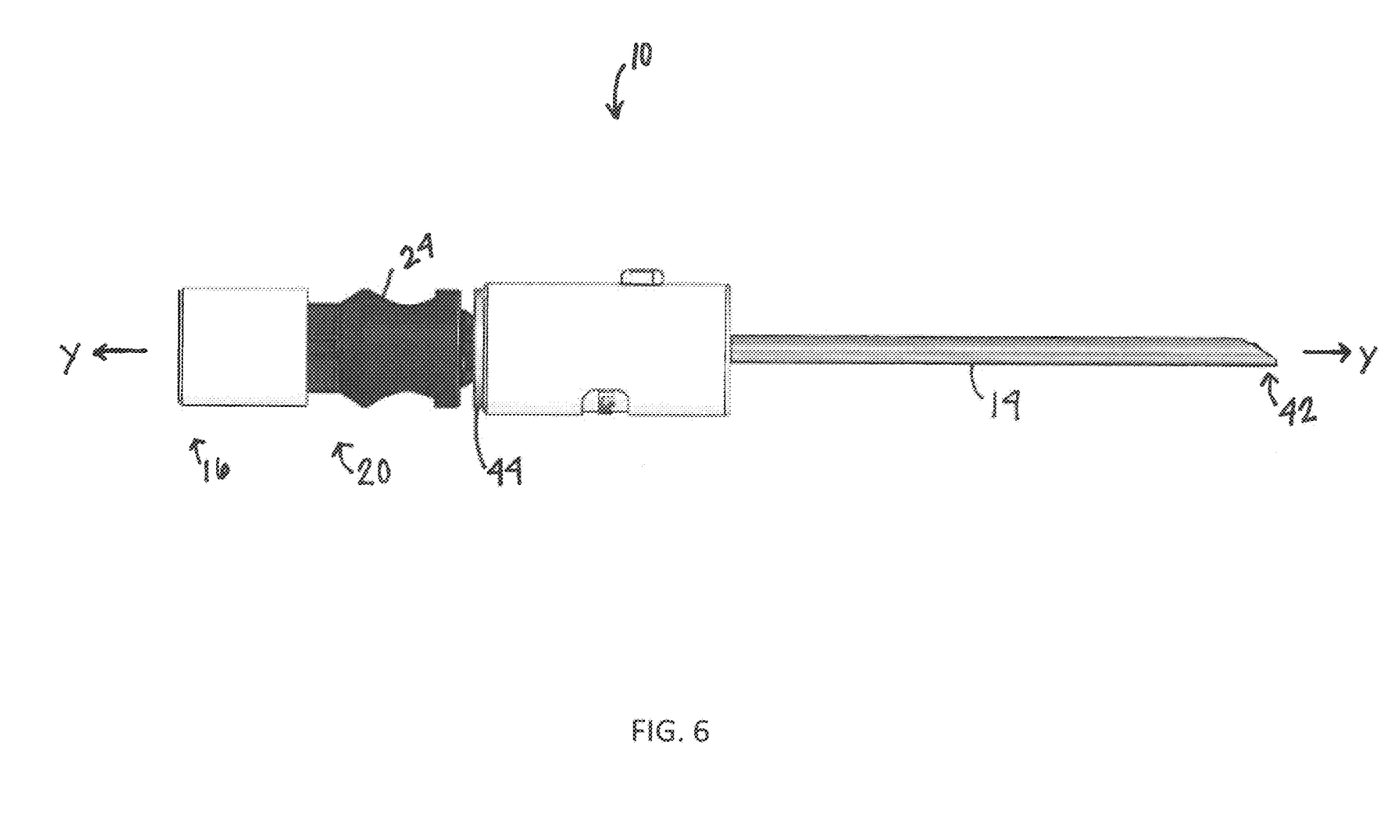
FIG. 6 is a side view schematic representation of the shaver bur in a retracted position, according to an embodiment.
Figure 7:
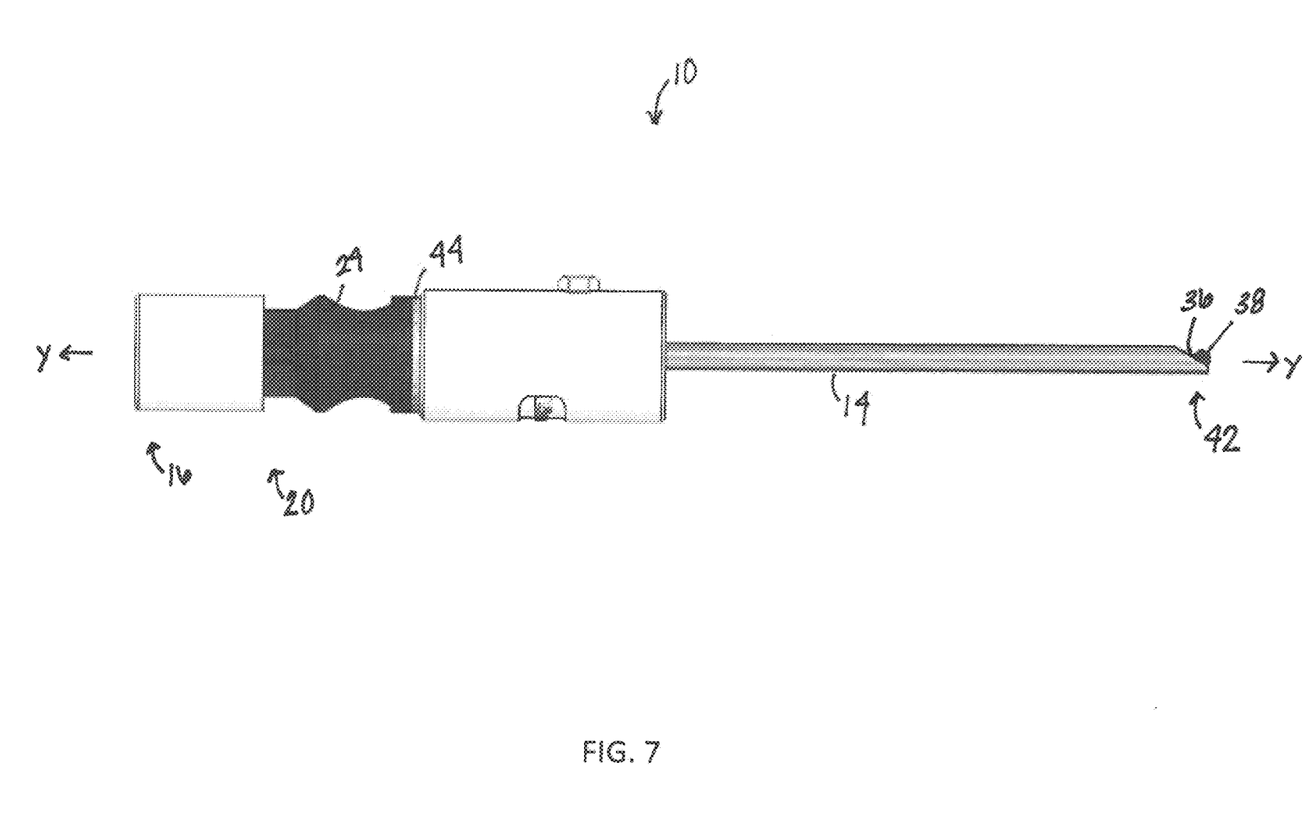
FIG. 7 is a side view schematic representation of the shaver bur in an extended position, according to an embodiment.

Turning now to FIGS. 6 and 7, there are shown side views schematic representations of the shaver bur 10 in a retracted position and an extended position, respectively, according to an embodiment. In the retracted position, the inner tube 36 with the distal bur tip 38 is retracted and protected within the outer tube 14, as shown in FIG. 6. From the retracted position, the twist ring 54 is rotated in a first direction (e.g., counter-clockwise). As the twist ring 54 rotates in the first direction, the inner assembly 20 moves axially along the central longitudinal y-y axis toward the distal end 42 of the outer tube 14, sliding the inner tube 36 distally from the outer tube 14. The twist ring 54 is rotated in the first direction until the bur tip 38 is exposed and ready for use, as shown in FIG. 7.

When use of the bur tip 38 is complete, the twist ring 54 is rotated in a second direction (e.g., clockwise). As the twist ring 54 rotates in the second direction, the twist ring 54 pushes against the one or more stems 48, which in turn, engage the inner assembly 20. Specifically, the stems 48 on the magnet retainer 44 are engaged and move axially and proximally along the central longitudinal y-y axis toward the proximal end 16 of the shaver bur 10. The magnet retainer 44 engages the inner hub 24, which is bonded to the inner tube 36. The entire inner assembly 20, including the bur tip 38, moves axially toward the proximal end 16 of the shaver bur 10. As a result, the bur tip 38 is fully retracted within the outer tube 14, as shown in FIG. 7.

The use of the twist ring 54 as the deployment mechanism allows the user to make fine-tune adjustments, permitting the bur tip to be completely exposed, fully retracted, or at some position therebetween. In an alternative embodiment, the twist ring 54 may also comprise a knob or other handle-like feature for rotating the twist ring 54. In another embodiment, the deployment mechanism 54 is a lever or latch assembly that, when moved from a first position to a second position, causes the bur tip 38 to move from the retracted position to the extended position. In yet another embodiment, the deployment mechanism 54 is an on/off button or an actuator button that when pressed, moves the bur tip 38 from the retracted position to the extended position. Similarly, the on/off button can operate such that it must be held down in the pressed state to maintain the bur tip 38 in the extended (or retracted) position. In an additional embodiment, the deployment mechanism 54 is a release ring that is pulled in the proximal direction to either move the outer tube 14 proximally over the inner tube 36, exposing the bur tip 38 or move the inner tube 36 in the distal direction out from the outer tube 14, exposing the bur tip 38. The release ring (and other embodiments of the deployment mechanism 54) can be used in conjunction with a locking mechanism that locks the shaver bur 10 in the retracted and/or extended positions.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A shaver bur, comprising:
    an inner assembly having an inner hub with an inner tube extending distally therefrom, the inner tube terminating in a distal bur tip;
    an outer assembly having an outer hub with an outer tube extending distally therefrom;
    wherein the inner tube is moveable within the outer tube between a retracted position and an extended position;
    a magnet retainer connected between the inner hub and the outer hub;
    a deployment mechanism connected to the outer hub, the deployment mechanism movable in a first direction and a second direction;
    wherein moving the deployment mechanism in the first direction moves the inner tube to the extended position and moving the deployment mechanism in the second direction moves the inner tube to the retracted position; and
    wherein moving the deployment mechanism in the second direction moves the deployment mechanism against the magnet retainer.

2. The system of claim 1, further comprising one or more slots extending at least partially through the outer hub.

3. The system of claim 2, further comprising one or more stems extending from the magnet retainer.

4. The system of claim 3, wherein each of the one or more stems extends through one of the one or more slots in the outer hub.

5. The system of claim 4, wherein the deployment mechanism abuts the one or more stems of the magnet retainer.

6. The system of claim 5, wherein the deployment mechanism is a disk rotatable in the first direction and the second direction.

* * * * *